(12) United States Patent
Gould

(10) Patent No.: US 10,070,853 B2
(45) Date of Patent: Sep. 11, 2018

(54) EXPANDABLE BALLOON DESUFFLATION ASSEMBLY

(71) Applicant: Covidien LP, Mansfield, MA (US)

(72) Inventor: Jessica Gould, North Haven, CT (US)

(73) Assignee: Covidien LP, Mansfield, MA (US)

( * ) Notice: Subject to any disclaimer, the term of this patent is extended or adjusted under 35 U.S.C. 154(b) by 1008 days.

(21) Appl. No.: 14/284,987

(22) Filed: May 22, 2014

(65) Prior Publication Data

US 2015/0051631 A1 Feb. 19, 2015

Related U.S. Application Data

(60) Provisional application No. 61/865,637, filed on Aug. 14, 2013.

(51) Int. Cl.
*A61B 17/02* (2006.01)
*A61B 17/32* (2006.01)
*A61B 17/00* (2006.01)

(52) U.S. Cl.
CPC ...... *A61B 17/0218* (2013.01); *A61B 17/0293* (2013.01); *A61B 2017/00287* (2013.01);
(Continued)

(58) Field of Classification Search
CPC ............ A61B 17/0218; A61B 17/0293; A61B 17/0281; A61B 17/22032; A61B 17/025;
(Continued)

(56) References Cited

U.S. PATENT DOCUMENTS

| 397,060 A | 1/1889 | Knapp |
| 512,456 A | 9/1894 | Sadikova |

(Continued)

FOREIGN PATENT DOCUMENTS

| EP | 480653 A1 | 4/1992 |
| EP | 0610099 A2 | 8/1994 |

(Continued)

OTHER PUBLICATIONS

European Office Action dated Nov. 2, 2016, issued in EP Application No. 14 180 769.3.

(Continued)

*Primary Examiner* — Elizabeth Houston
*Assistant Examiner* — Socrates L Boutsikaris

(57) ABSTRACT

A balloon dissector includes a cannula, an expandable bladder, and a cord. The cannula defines a lumen between proximal and distal ends. The expandable bladder is configured to expand when fluid is injected into the lumen and includes an inner surface, a proximal base, and a retainer. The proximal base is selectively coupleable to the distal end of the cannula in a sealing relationship. The retainer is positioned on the inner surface of the expandable bladder. The cord includes a first end, a second end, and a central portion. The one end of the cord extends from the proximal end of the cannula. The cord extends through the lumen of the cannula and through the retainer of the bladder returning into the lumen. The cord configured to draw the expandable bladder into the lumen after the expandable bladder is expanded.

12 Claims, 7 Drawing Sheets

(52) U.S. Cl.
CPC .............. *A61B 2017/00557* (2013.01); *A61B 2017/320048* (2013.01)

(58) Field of Classification Search
CPC ........... A61B 2017/00287; A61B 2017/00557; A61B 2017/320048; A61B 2017/320044; A61B 2017/00535; A61B 2017/0225; A61B 2017/0287; A61B 2017/22001; A61B 2017/22051; A61B 2017/22061; A61B 2017/22062; A61B 2017/22065; A61B 90/02; A61B 1/32; A61M 2025/1084; A61M 2025/1093; A61M 25/005; A61M 25/04; A61M 25/0074
USPC ................. 606/190–200; 600/201, 207–208; 604/96.01, 103.08, 103.09, 338, 339
See application file for complete search history.

(56) References Cited

U.S. PATENT DOCUMENTS

| | | | |
|---|---|---|---|
| 1,213,005 A | 1/1917 | Pillsbury | |
| 2,912,981 A | 11/1959 | Keough | |
| 2,936,760 A | 5/1960 | Gains | |
| 3,039,468 A | 6/1962 | Price | |
| 3,050,066 A | 8/1962 | Koehn | |
| 3,168,092 A * | 2/1965 | Silverman | A61B 1/00151 600/114 |
| 3,253,594 A | 5/1966 | Matthews et al. | |
| 3,397,699 A | 8/1968 | Kohl | |
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,479,497 A | 10/1984 | Fogarty et al. | |
| 4,485,805 A | 12/1984 | Foster, Jr. | |
| 4,490,137 A | 12/1984 | Moukheibir | |
| 4,496,345 A | 1/1985 | Hasson | |
| 4,526,175 A | 7/1985 | Chin et al. | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A | 4/1990 | Haindl | |
| 4,931,042 A | 6/1990 | Holmes et al. | |
| 4,946,440 A * | 8/1990 | Hall | A61B 18/08 600/569 |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,250,025 A | 10/1993 | Sosnowski et al. | |
| 5,258,026 A | 11/1993 | Johnson et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,480 A | 9/1997 | Knight et al. | |
| 5,667,520 A | 9/1997 | Bonutti | |
| 5,690,668 A | 11/1997 | Fogarty et al. | |
| 5,695,514 A | 12/1997 | Chin | |
| 5,702,416 A | 12/1997 | Kieturakis et al. | |
| 5,704,372 A | 1/1998 | Moll et al. | |
| 5,707,382 A | 1/1998 | Sierocuk et al. | |

(56) References Cited

U.S. PATENT DOCUMENTS

| | | |
|---|---|---|
| 5,713,869 A | 2/1998 | Morejon |
| 5,722,934 A | 3/1998 | Knight et al. |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,814,059 A | 9/1998 | Hart et al. |
| 5,814,060 A | 9/1998 | Fogarty et al. |
| 5,836,913 A | 11/1998 | Orth et al. |
| 5,836,961 A | 11/1998 | Kieturakis et al. |
| RE36,043 E | 1/1999 | Knighton |
| 5,865,802 A | 2/1999 | Yoon et al. |
| 5,873,889 A | 2/1999 | Chin |
| 5,893,866 A | 4/1999 | Hermann et al. |
| 5,902,316 A | 5/1999 | Mollenauer |
| 5,904,699 A | 5/1999 | Schwemberger et al. |
| 5,925,058 A | 7/1999 | Smith et al. |
| 5,968,066 A | 10/1999 | Fogarty et al. |
| 6,013,090 A | 1/2000 | Fogarty et al. |
| 6,036,714 A | 3/2000 | Chin |
| 6,102,928 A | 8/2000 | Bonutti |
| 6,152,895 A | 11/2000 | Wilk |
| 6,168,608 B1 | 1/2001 | Echeverry et al. |
| 6,312,442 B1 | 11/2001 | Kieturakis et al. |
| 6,361,543 B1 | 3/2002 | Chin et al. |
| 6,368,337 B1 | 4/2002 | Kieturakis et al. |
| 6,432,121 B1 | 8/2002 | Jervis |
| 7,300,448 B2 | 11/2007 | Criscuolo et al. |
| 7,311,719 B2 | 12/2007 | Bonutti |
| 7,744,617 B2 | 6/2010 | Lunsford et al. |
| 8,500,770 B2 | 8/2013 | Echevery et al. |
| 8,540,745 B2 | 9/2013 | Criscuolo et al. |
| 2003/0004529 A1 | 1/2003 | Tsonton et al. |
| 2007/0028923 A1 | 2/2007 | Souris et al. |
| 2007/0078477 A1 | 4/2007 | Heneveld et al. |
| 2009/0182368 A1 | 7/2009 | Lunsford et al. |
| 2012/0203220 A1 | 8/2012 | Brannan et al. |
| 2012/0303018 A1 | 11/2012 | Ladtkow et al. |
| 2013/0046332 A1 | 2/2013 | Jones et al. |

FOREIGN PATENT DOCUMENTS

| | | |
|---|---|---|
| JP | 2008067994 A | 3/2008 |
| WO | 8200408 A1 | 2/1982 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9324172 A1 | 12/1993 |
| WO | 9713464 A2 | 4/1997 |
| WO | 9838920 A1 | 9/1998 |
| WO | 9912602 A1 | 3/1999 |
| WO | 0296307 A2 | 12/2002 |
| WO | 2011128622 A1 | 10/2011 |
| WO | 201204739 A2 | 1/2012 |
| WO | 2012047939 A2 | 4/2012 |

OTHER PUBLICATIONS

European Search Report dated Feb. 24, 2015 issued in European Appln. No. 14180769.

European Office Action dated Mar. 2, 2016, issued in European Application No. 14180769.3.

Chinese Office Action dated Jun. 1, 2018 in CN Appln. No. 201410400382.

* cited by examiner

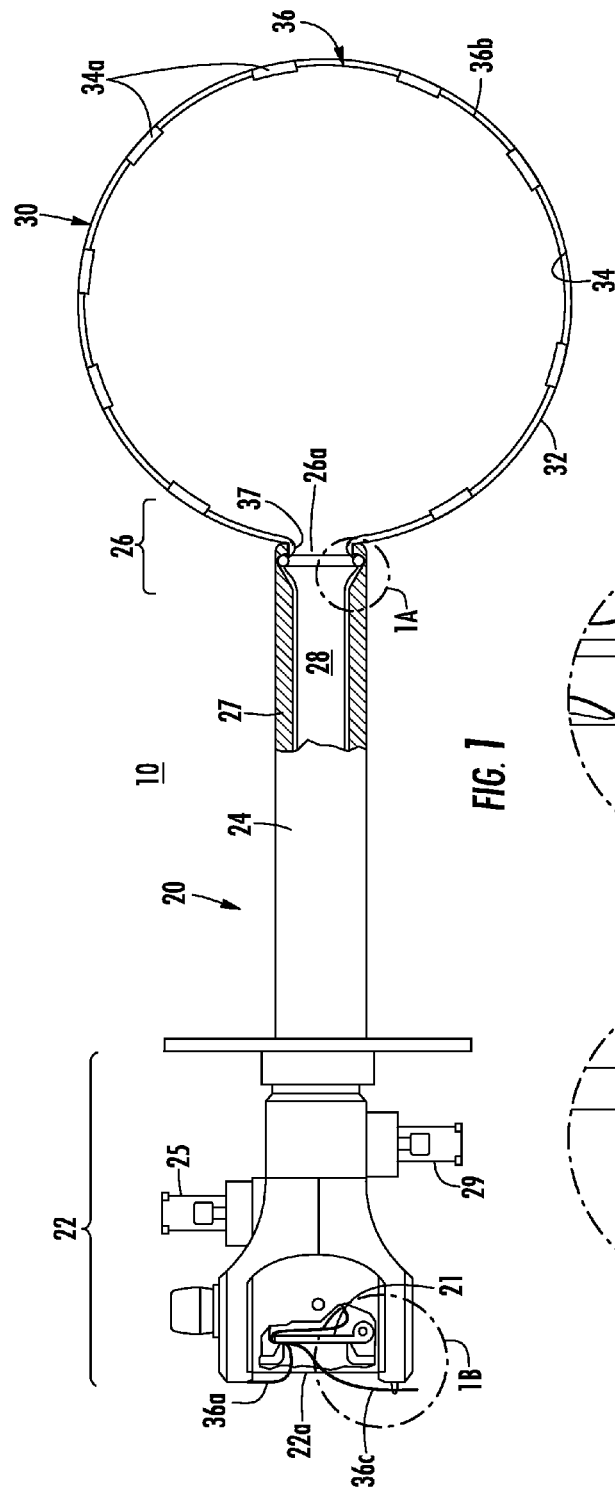
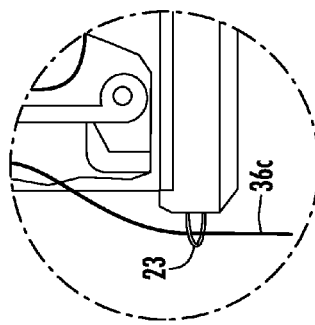
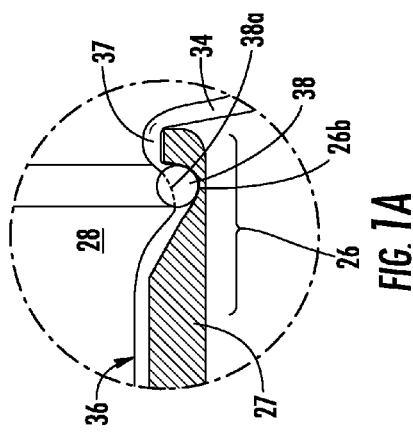
FIG. 1
FIG. 1A
FIG. 1B

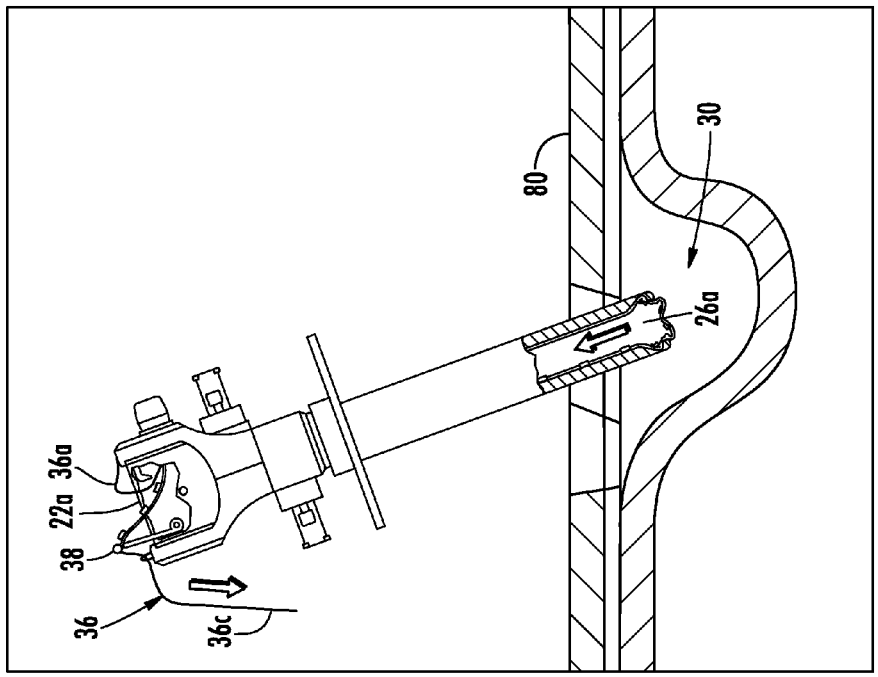
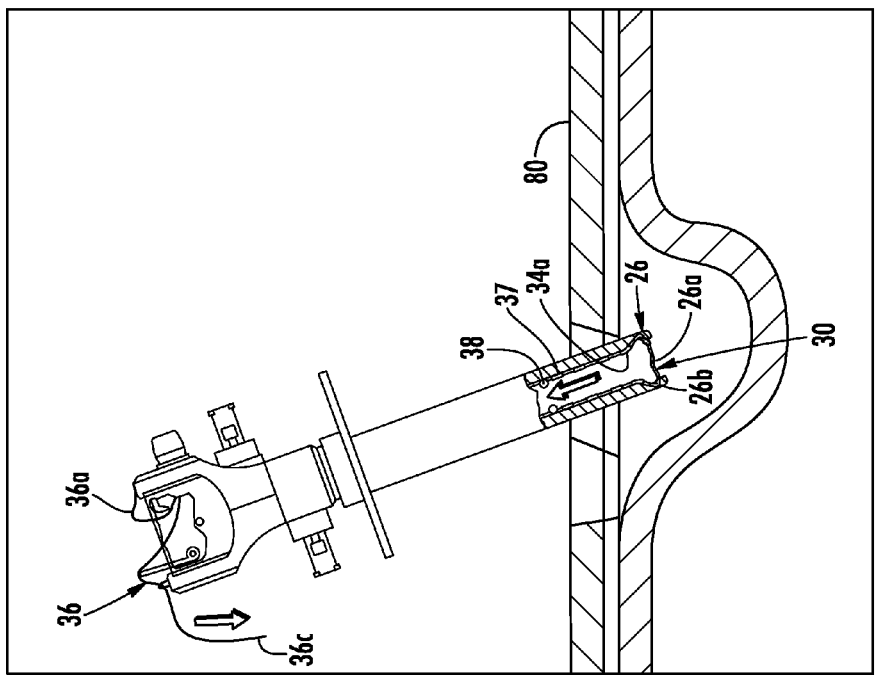

EXPANDABLE BALLOON DESUFFLATION ASSEMBLY

CROSS-REFERENCE TO RELATED APPLICATIONS

This application claims the benefit of and priority to U.S. Provisional Patent Application No. 61/865,637, filed Aug. 14, 2013, the entire disclosure of which is incorporated by reference herein.

BACKGROUND

1. Technical Field

The present disclosure relates to medical devices, and particularly to fluid expandable medical devices such as cannulas, catheters, dissectors, retractors, and similar devices including a desufflation mechanism.

2. Discussion of Related Art

Tissue dissectors are used for separating tissues in order to create a space between tissue layers and tissue retractors are used to expand a space between organs and/or tissue layers. The space created and/or expanded is used to improve visualization and to increase working space during open surgery and/or minimally invasive surgery. Fluid expandable balloon devices allow a surgeon to take potential spaces within the body and turn them into existing spaces safely, easily, and controllably in order to safely visualize appropriate tissue and/or operate. Such devices allow for selective dissection and/or retraction of tissue, either of hard tissue such as bone or soft tissue planes, to be moved out of the way to improve working space and visualization, which is of particular benefit while operating from within the body, e.g., minimally invasive surgery. These fluid expandable balloon devices also permit working within the body without damaging a great deal of tissue in the path between a skin opening and the working area, by minimizing the external orifice or skin incision. Although such devices have achieved relative levels of success, improvements to such fluid expandable balloon devices would be advantageous. For example, an active means for desufflating a fluid expandable balloon device and removing the bladder from the surgical space.

SUMMARY

In an aspect of the present disclosure, a balloon dissector includes a cannula, an expandable bladder, and a cord. The cannula defines a lumen extending between proximal and distal ends of the cannula. The expandable bladder is configured to expand when a fluid is injected into the lumen. The bladder includes an inner surface, a proximal base, and a retainer. The proximal base is selectively coupled in a sealing relationship to the distal end of the cannula. The retainer is positioned on the inner surface of the bladder. The cord has a first end, a second end, and a central portion. One of the first and second ends extends from the proximal end of the cannula. The central portion extends from the first end to the second end through the lumen and through the retainer of the bladder. The cord is configured to draw a portion of the bladder into the lumen after the bladder is deflated. The central portion of the cord can draw the deflated bladder into the lumen. The first end of the cord can be affixed to the proximal end of the cannula. In embodiments, the first end of the cord is affixed to an inner surface of the cannula. The proximal end of the cannula can include retaining mechanism. The retaining mechanism is configured to slidably receive the second end of the cord therein. The second end of the cord can slidably pass through the clamp. In some embodiments, the distal end of the cannula includes a recess configured to receive an expandable ring. The expandable ring is configured to retain the proximal base of the bladder in a sealing relationship with the proximal end of the cannula. The expandable ring can include a passage to slidably receive the cord. The expandable ring can be integrally formed in the proximal base of the bladder.

In another aspect of the present disclosure, a method of dissecting tissue layers includes inserting a balloon dissector into a surgical site between two tissue layers, dissecting the tissue layers by expanding a bladder with an inflation fluid, and withdrawing at least a portion of the bladder into a lumen of the cannula by pulling a portion of a cord. The balloon dissector can include a cannula, an expandable bladder, and the cord. Dissecting the tissue layers can include deflating the bladder by pulling an end of the cord, repositioning the cannula, and reinflating the bladder with the inflation fluid. Deflating, repositioning, and reinflating can be repeated until a desired space is formed between the tissue layers. The method may further include selecting the inflation fluid from the group consisting of air, nitrogen, and saline. The method may include removing the bladder from the proximal end of the cannula. The method may include inserting a surgical instrument through the lumen of the cannula.

In yet another aspect of the present disclosure, an expandable bladder for dissecting and/or retracting tissue is configured for use with an introducer. The expandable bladder includes a proximal base, an inner surface, at least one retainer, and a cord. The introducer can be a cannula as described herein. The proximal base is sized and configured to engage the introducer. The proximal base can engage the introducer in a sealing relationship. The cord has a first end, a second end, and a central portion. The central portion of the cord is slidably received by the at least one retainer. The expandable bladder has an inflated condition having a first volume and a deflated condition having a second volume. In the inflated condition, the expandable bladder has a first volume and in the deflated condition, the expandable bladder has a second volume. The second volume can be smaller than the first volume. The cord is configured to transition the expandable bladder from the inflated condition to the deflated condition. In embodiments, the expandable bladder forms a spherical enclosure and the at least one retainer includes a plurality of retainers around a circumference of the inner surface. In some embodiments, the expandable bladder forms a toroidal enclosure and the at least one retainer includes a central hole through the expandable bladder. In certain embodiments, the expandable bladder forms a triangular enclosure, the at least one retainer includes a connector positioned at each corner of the triangular enclosure, and the proximal base is positioned orthogonal to the triangular-shaped enclosure.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 1 is a partial cutaway of a fluid expandable balloon dissector provided in accordance with the present disclosure including a desufflation cord;

FIGS. 1A and 1B are enlargements of the detail areas 1A and 1B shown in FIG. 1;

FIGS. 2-8 are a progression of side views showing the balloon dissector of FIG. 1 being used to dissect tissue layers;

DETAILED DESCRIPTION

Figure 3:
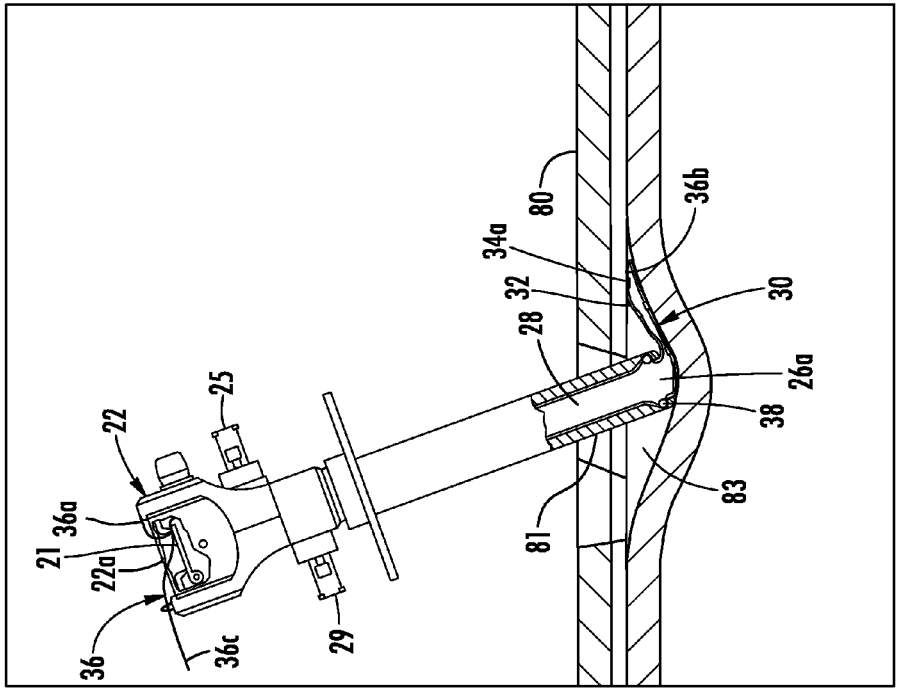

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician.

While the fluid expandable balloon device described in detail below is a fluid expandable balloon dissector, it will be appreciated by a person skilled in the art that the fluid expandable balloon device is adaptable to a fluid expandable retraction device or other similar fluid expandable surgical devices that include fluid expandable balloons.

Referring now to FIG. 1, a fluid expandable balloon dissector 10 is provided in accordance with the present disclosure incorporating a cannula 20 and a bladder 30. Cannula 20 has a proximal portion 22 near an open proximal end 22a, an elongated tubular body 24 extending distally from proximal portion 22, and a distal portion 26 near an open distal end 26a of the elongated tubular body 24. Elongated tubular body 24 has an outer wall 27 defining a central lumen 28 between proximal end 22a and distal end 26a.

With additional reference to FIG. 1A, expandable bladder 30 includes an outer surface 32 and an inner surface 34. Inner surface 34 can include retainers 34a that slidably receive cord 36. Cord 36 is operatively associated with inner surface 34 such that cord 36 can manipulate the size and/or shape of bladder 30. As will be appreciated by those skilled in the art, cord 36 may be of any known material or construction, including but not limited to fabric, plastic, latex and elastomeric materials, and may include any number of segments or fibers, including braided constructions. A proximal base 37 of bladder 30 is releasably coupled to proximal portion 26 of cannula 20. In embodiments, proximal base 37 is releasably coupled to proximal portion 26 by an expandable ring 38 seated in a recess 26b formed in proximal portion 26 as shown in FIG. 1A. Cord 36 can be coupled to an outer surface of expandable ring 38. Expandable ring 38 can include a passage 38a which slidably receives cord 36 therethrough. In some embodiments, expandable ring 38 is integrally formed into proximal base 37 of bladder 30.

Referring also to FIG. 1B, cord 36 has a first end 36a, a central portion 36b, and a second end 36c. First and second ends 36a, 36c extend into proximal portion 22 of cannula 20 and through lumen 28 of elongated tubular body 24. In embodiments, first and/or second end 36a, 36c are positioned proximal to proximal end 22a of cannula 20. In the embodiment shown, central portion 36b of cord 36 extends distally from first end 36a through central lumen 28, into distal portion 26 of cannula 20 through distal end 26a, and into bladder 30. Central portion 36b of cord 36 passes through retainer 34a in inner surface 34 of bladder 30. Central portion 36b reenters cannula 20 through distal end 26a after passing though retainer 34a. Central portion 36b extends proximally from distal end 26a through central lumen 28 to proximal portion 22 of cannula 20 to second end 36c of cord 36. First end 36a and/or second end 36c can be affixed within lumen 28 in proximal portion 22 of cannula 20. In embodiments, first and/or second end 36a, 36c is slidably received in a retaining mechanism such as clamp 23 positioned in proximal portion 22 of cannula 20. Clamp 23 can be positioned at proximal end 22a of cannula 20 as shown in FIG. 1B. As will be appreciated by those skilled in the art, retaining mechanism 23 may comprise a variety of constructions, including loops, hooks, and shoulders.

Figure 2:
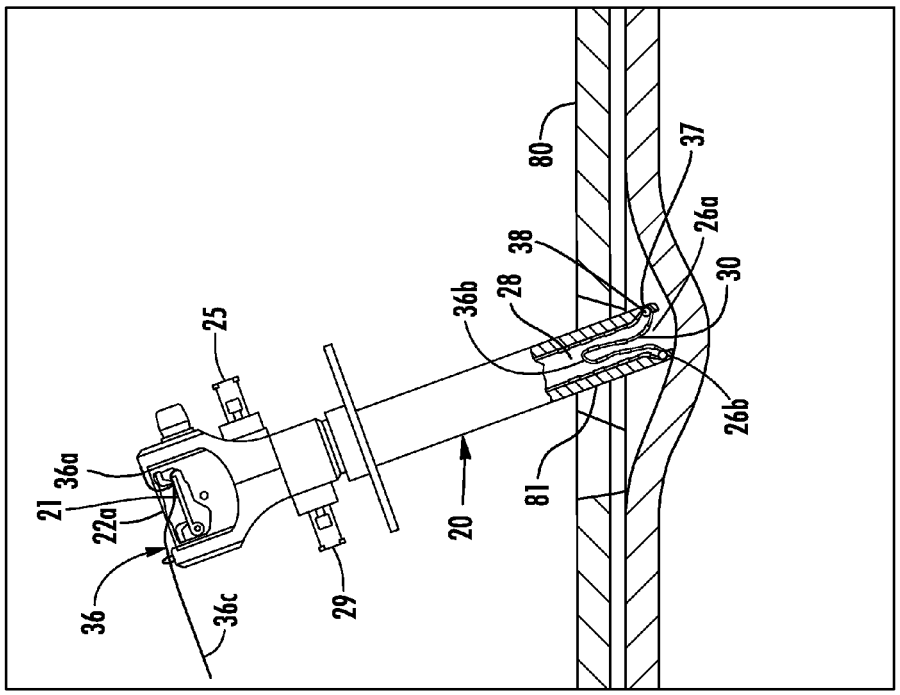

With reference to FIGS. 2-8, the use of fluid expandable balloon dissector 10 will now be described in detail. Bladder 30 is disposed substantially within central lumen 28 of cannula 20, proximal base 37 of bladder 30 is coupled in a sealing relationship with distal portion 26 of cannula 20, and first and second ends 36a, 36c of cord 36 are positioned near proximal end 22a as shown in FIG. 2. When bladder 30 is at least partially deflated, surgical instrument 10 is slidable through a surgical site 81 in tissue layer 80 of a patient. Surgical site 81 can be a naturally occurring orifice or an incision in a tissue layer. Surgical instrument 10 can be slid through a port of an access device (not shown) or inserted directly through surgical site 81.

Referring to FIG. 3, inflation fluid (not shown) is introduced into central lumen 28 through inflation port 29. The inflation fluid can be air, nitrogen, saline, or any other suitable fluid. The inflation fluid can be gas, liquid, or a combination thereof. A valve member 21 in the proximal portion 22 of cannula 20 is closed when the inflation fluid is being introduced into central lumen 28. As the inflation fluid is introduced into central lumen 28, pressure increases in central lumen 28 and bladder 30 such that expandable bladder 30 extends distally through distal end 26a of cannula 20 and into body cavity 83. When expandable bladder 30 extends from distal end 26a, expandable bladder 30 is positioned near tissue and/or organs to be dissected and/or retracted. As expandable bladder 30 extends, central portion 36b of cord 36 cooperates with retainer 34a on inner surface 34 to extend expandable bladder 30 from distal end 26a.

Figure 4:
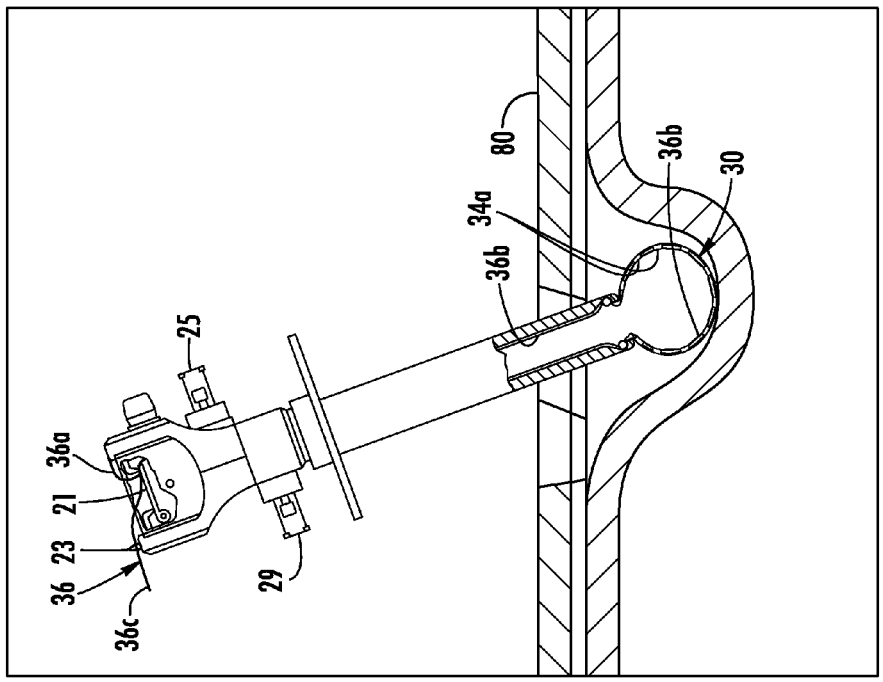

Referring to FIG. 4, as additional inflation fluid is introduced through inflation port 29 to inflate bladder 30, the tissue and/or organs are dissected and/or retracted. When bladder 30 is inflated, bladder 30 can maintain the tissue and/or organs in a desired position to provide access and/or visibility to underlying tissue and/or organs.

Figure 5:
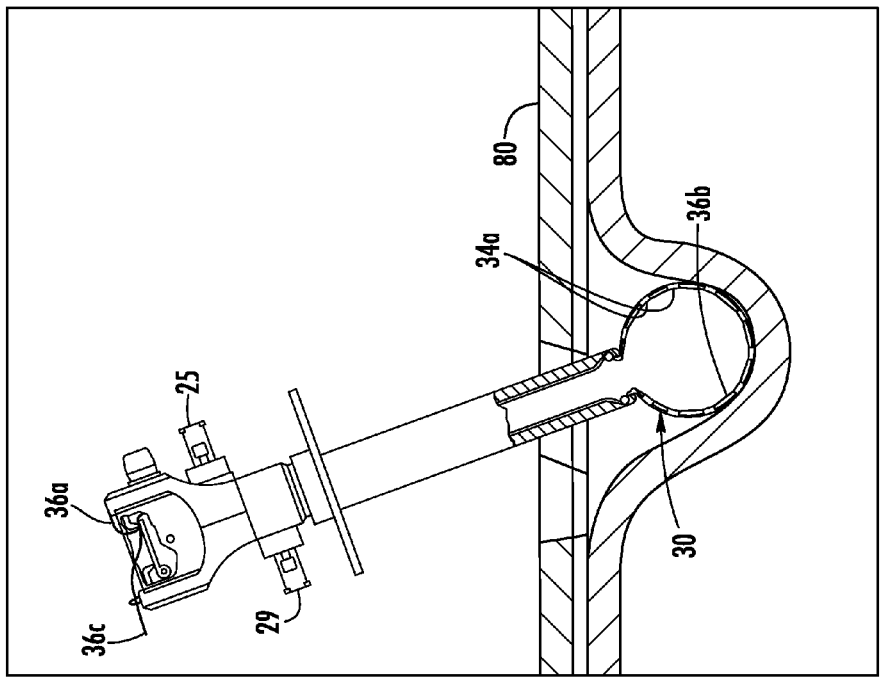

Referring to FIG. 5, bladder 30 is deflated allowing the tissue and/or organs to at least partially return to the position each was in before being dissected and/or retracted. Inflation fluid can be released by opening valve member 21 and/or deflation port 25. The pressure of the tissue and/or organs acting on bladder 30 to at least partially deflate bladder 30. Bladder 30 can be repositioned and reinflated after being partially retracted or fully retracted as described below. First and/or second end 36a, 36c can be pulled to partially retract and/or shape bladder 30. For example, if first end 36a is affixed to proximal end 22a and second end 36c is slidably received within clamp 23, second end 36c is pulled such that central portion 36b of cord 36 engages retainers 34a to partially retract bladder 30. It will be appreciated that the position and number of retainers 34a can determine the shape of and retraction of bladder 30 when cord 36 is pulled.

Referring to FIG. 6, first and/or second end 36a, 36c of cord 36 are further pulled to retract bladder 30 into cannula 20. Continuing the example above, second end 36c is pulled such that central portion 36b of cord 36 draws retainers 34a and bladder 30 through distal end 26a and into cannula 20. Further pulling of second end 36c draws bladder 30 through proximal end 22a of cannula 20 as shown in FIG. 7. As second end 36c is pulled, proximal base 37 of bladder 30 is decoupled from distal portion 26 of cannula 20. In embodiments, proximal base 37 separates from distal portion 26. It will be appreciated that when proximal base 37 separates from distal portion 26, bladder 30 will rapidly desuffalate when valve member 21 and/or deflation port 25 are closed. In some embodiments, bladder 30 pulls on proximal base 37 to disengage proximal base 37 from expandable ring 38. In embodiments where cord 36 passes through passages 38a (FIG. 1A) in expandable ring 38, cord 36 disengages expandable ring 38 from distal portion 26 of cannula 20.

Figure 8:
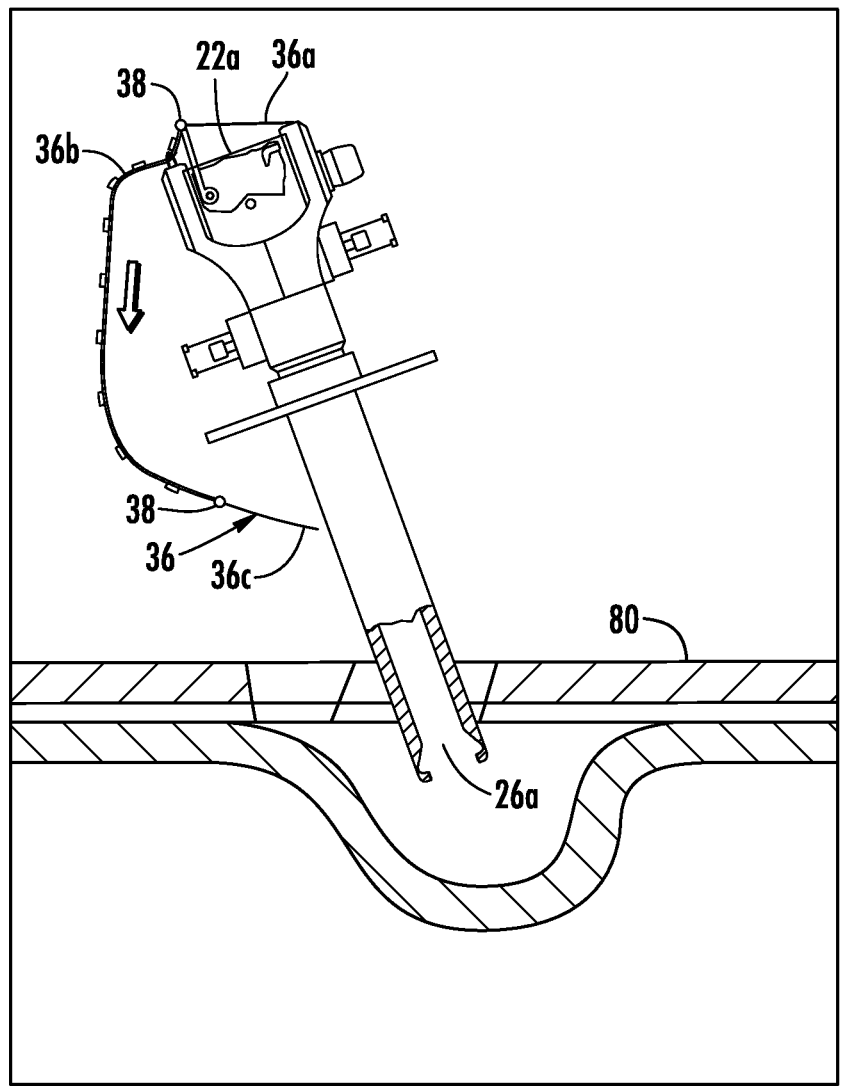

Referring to FIG. 8, bladder 30 can be completely withdrawn from cannula 20 while instrument 10 is inserted within body cavity 83 permitting introduction of additional instruments into body cavity 83 through cannula 20. In embodiments, proximal portion 22 includes a sealing member to engage the body of additional surgical instruments (not shown). In some embodiments, proximal portion 22 of cannula 20 is releasably coupled to elongated tubular body 24 such that when bladder 30 is withdrawn from instrument 10, proximal portion 22 is separated from elongated tubular body 24 permitting a second proximal portion (not shown) to be coupled to elongated tubular body 24. The second proximal portion can be at least one of a seal housing, an obturator, etc.

In embodiments, retainers 34a form a continuous sleeve around inner surface 34 and cord 36 is disposed within the sleeve formed by retainers 34a. In some embodiments, a rib (not shown) is formed in inner surface 34 having openings (not shown) and cord 36 laces through the openings. In certain embodiments, cord 36 is affixed to inner surface 34.

Figure 9A:
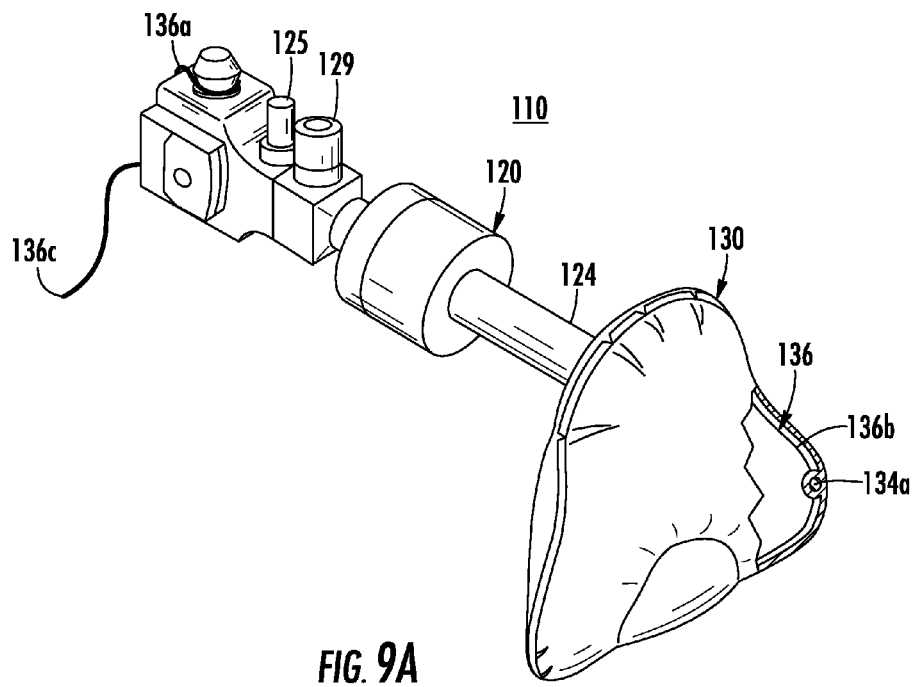
FIGS. 9A and 9B are perspective views of other fluid expandable balloon devices in accordance with the present disclosure.
Figure 9B:
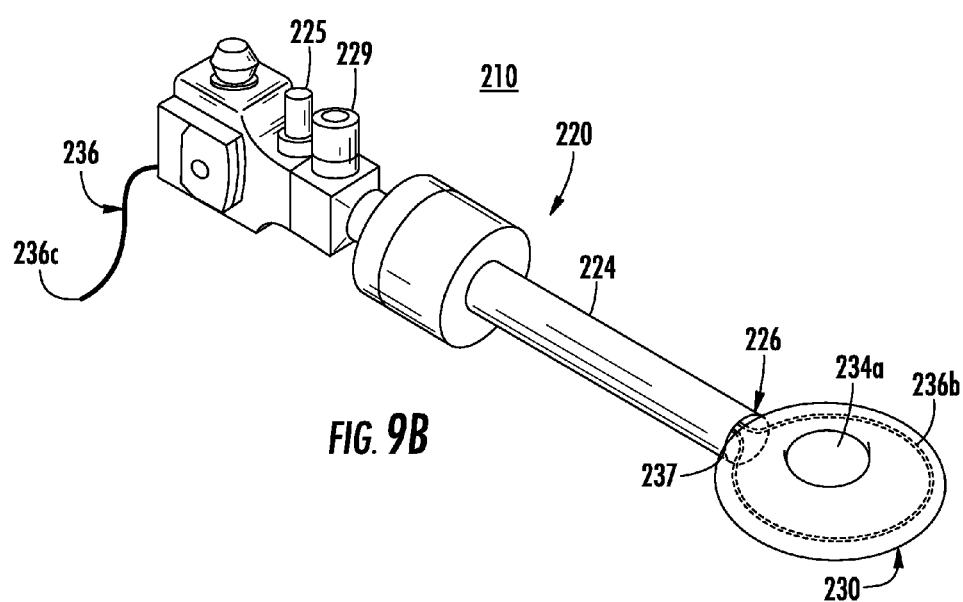

Referring to FIGS. 9A and 9B, additional fluid expandable balloon devices 110, 210 are provided in accordance with the present disclosure each including a cannula 120, 220, a bladder 130, 230, and a cord 136, 236. Fluid expandable balloon devices 110 and 210 are substantially similar to dissector 10 (FIG. 1) with similar structures labeled with similar identifiers with a "1" or a "2" preceding the previous label respectively.

Fluid expandable balloon device 110 is triangular dissector including a bladder 130 having retainers 134a positioned about the edge of bladder 130.

Fluid expandable balloon device 210 is a toroidal retractor including a bladder 230 having a central hole 234a through the center of bladder 230. Cord 236 of fluid expandable balloon device 210 includes a central portion 236b within bladder 230 which surrounds central hole 234a. When central portion 236b is retracted it can engage the inner surface of central hole 234a to withdraw bladder 230 within and through a cannula 220 such that central hole 234a acts as a retainer. In some embodiments, central portion 236b is attached to retainers (not shown) in the inner surface of bladder 230 similar to central portion 36b (FIG. 1) of fluid expandable balloon dissector 10 (FIG. 1).

Figure 10:
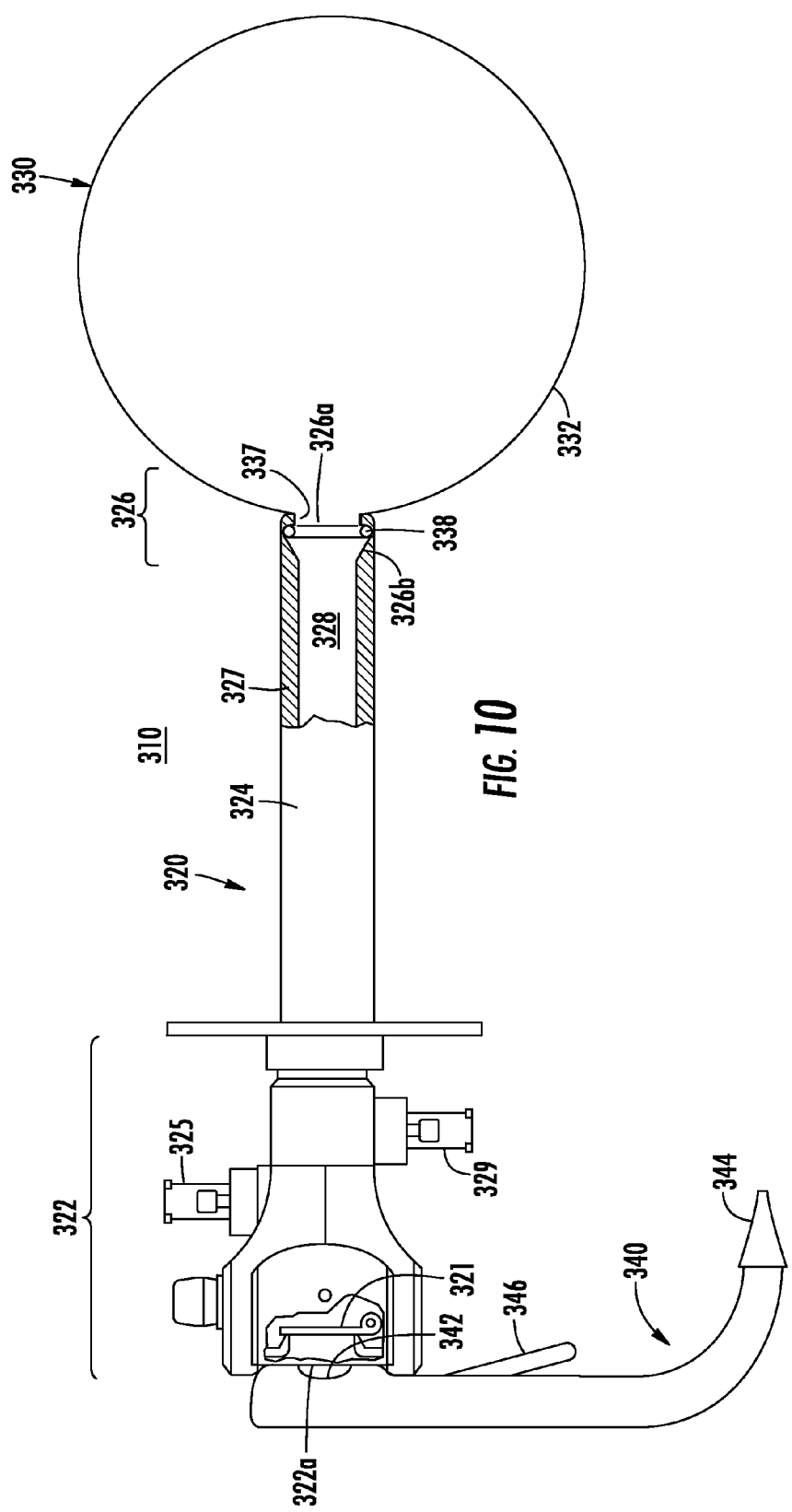
FIG. 10 is a partial cutaway of another fluid expandable balloon dissector provided in accordance with the present disclosure including a vacuum desufflator.

Referring to FIG. 10, another fluid expandable balloon dissector 310 is provided in accordance with the present disclosure including a cannula 320, a bladder 330, and a vacuum desufflator 340. Fluid expandable balloon device 310 is substantially similar to dissector 10 (FIG. 1) with similar structures labeled with similar identifiers with a "3" preceding the previous label.

Bladder 330 includes a proximal base 337 releasably coupled to a distal portion 326 of cannula 320. In embodiments, proximal base 337 is releasably coupled to distal portion 326 by an expandable ring 338 seated in a recess 326b formed in distal portion 326. In some embodiments, expandable ring 338 is integrally formed into proximal base 337 of bladder 330.

Vacuum desufflator 340 includes a nozzle 342 and a proximal connector 344. Nozzle 342 is positioned at the distal end of vacuum desufflator 340 and is configured to sealing engage a proximal end 322a of cannula 320. Proximal connector 344 is configured to couple to a vacuum source (not shown), e.g., a vacuum source commonly available in a surgical environment. Vacuum desufflator 340 can include an actuator 346 configured to control the vacuum or suction at nozzle 342. Actuator 346 can be an analog switch or a binary switch.

Vacuum desufflator 340 may be used to deflate bladder 330 and/or withdraw bladder through proximal end 322a of cannula 320. Nozzle 342 is positioned over proximal end 322a of cannula 320 such that nozzle 342 sealingly engages proximal end 322a of cannula 320. Suction from nozzle 342 deflates bladder 330. Additional suction from nozzle 342 draws bladder 330 through cannula 320 such that proximal base 337 separates from distal portion 326 of cannula 320 as bladder 330 is drawn to nozzle 342. Bladder 330 may be drawn through nozzle 342. In embodiments, bladder 330 seals nozzle 342 such that as nozzle 342 disengages proximal end 322a of cannula 320, bladder 330 is removed from proximal end 322a.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed:

1. A balloon dissector comprising:
    a cannula defining a lumen extending between proximal and distal ends thereof;
    an expandable bladder configured to expand when fluid is injected into the lumen, the bladder including:
        an inner surface;
        a proximal base selectively coupled to the distal end of the cannula in a sealing relationship; and
        a retainer formed on the inner surface of the bladder; and
    a cord having a first end, a second end, and a central portion, second end extending proximally from the proximal end of the cannula, the central portion extending from the first end to the second end through the lumen and through the retainer of the bladder, the retainer positioned distal of the first end of the cord when the bladder is inflated, the cord configured to draw a portion of the bladder into the lumen after the bladder is deflated.

2. The dissector of claim 1, wherein the central portion of the cord is configured to draw the portion of the bladder into the lumen after the bladder is deflated.

3. The dissector of claim 2, wherein the central portion of the cord is configured to draw the bladder through the proximal end of the cannula after the bladder is deflated.

4. The dissector of claim 1, wherein the first end of the cord is affixed to the proximal end of the cannula.

5. The dissector of claim 1, wherein the first end of the cord is affixed to an inner surface of the cannula.

6. The dissector of claim 1, wherein the proximal end of the cannula includes a retaining mechanism, wherein the retaining mechanism is configured to slidably receive the second end of the cord therein.

7. The dissector of claim 1, wherein the distal end of the cannula includes a recess configured to receive an expandable ring, the expandable ring configured to retain the proximal base of the bladder in the sealing relationship with the proximal end of the cannula.

8. The dissector of claim 7, wherein the expandable ring includes a passage configured to slidably receive the cord.

9. The dissector of claim 7, wherein the expandable ring is integrally formed in the proximal base of the bladder.

10. The dissector of claim 1, wherein the retainer is positioned distal of the proximal base of the bladder when the bladder is fully expanded.

11. The dissector of claim 1, wherein the retainer is spaced apart along the inner surface of the bladder from the proximal base of the bladder.

12. The dissector of claim 1, wherein the central portion of the cord is slidably received in the retainer of the bladder.

* * * * *

UNITED STATES PATENT AND TRADEMARK OFFICE
CERTIFICATE OF CORRECTION

| | |
|---|---|
| PATENT NO. | : 10,070,853 B2 |
| APPLICATION NO. | : 14/284987 |
| DATED | : September 11, 2018 |
| INVENTOR(S) | : Gould |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this
Twenty-seventh Day of August, 2019

Andrei Iancu
*Director of the United States Patent and Trademark Office*